Figure 1:
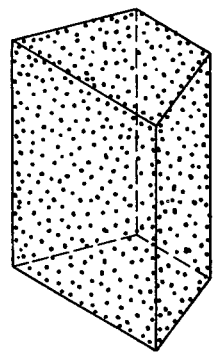

United States Patent [19]

Wegner

[11] 3,965,577
[45] June 29, 1976

[54] PELLETS

[75] Inventor: Günther Wegner, Neuenhain, Taunus, Germany

[73] Assignee: Hoechst Aktiengesellschaft, Frankfurt am Main, Germany

[22] Filed: May 15, 1974

[21] Appl. No.: 470,317

Related U.S. Application Data

[62] Division of Ser. No. 323,434, Jan. 15, 1973, abandoned.

[30] Foreign Application Priority Data

Jan. 13, 1972 Germany.................... 7201061[U]

[52] U.S. Cl................................................ 32/40 R
[51] Int. Cl.².......................................... A61C 3/00
[58] Field of Search............ 128/2.05 N, 2 N, 260, 128/269, 270; 32/40 R

[56] References Cited

UNITED STATES PATENTS

| | | | |
|---|---|---|---|
| 2,305,367 | 12/1942 | Webb.................................. | 128/2 N |
| 3,508,547 | 4/1970 | Deuschle........................... | 128/269 |
| 3,749,094 | 7/1973 | Duncan.............................. | 128/270 |

*Primary Examiner*—Robert Peshock
*Attorney, Agent, or Firm*—Curtis, Morris & Safford

[57] ABSTRACT

Pellets which are manufactured from an elastic soft cellular plastics material having open pores of a volumetric weight of from 25 to 40 kg/m³ and having a number of 10 to 20/cm useful in a method for determining the vitality of tooth's pulpa.

4 Claims, 3 Drawing Figures

U.S. Patent   June 29, 1976   3,965,577

PELLETS

This application is a divisional application of Ser. No. 323,434 filed Jan. 15, 1973 and now abandoned.

The present invention relates to pellets.

These pellets are manufactured by means of a cellular plastics material which has a volumetric weight of about 25 to 40 kg/m$^3$ and a number of pores of about 10 to 20/cm.

In dental diagnosis it is of main importance to ascertain the vitality of the pulpa. In this field cold-producing agents, for example, difluorodichloromethane, have also been used in recent times besides of electrotesting methods and carbon dioxide snow. This agent allows a very exact diagnosis by spraying it directly on the tooth to test. Direct spraying must only be carried out if the preceding examination of the tooth by touching it with the cold-producing agent shows a negative result. To carry out the examination by touch, the cold-producing agent is sprayed on a pellet which is promptly contacted with the tooth after its impregnation. For this indirect method, cellulose or cotton-wool tampons used for decades in dental practice are not suitable because they can stick to the tooth by freezing on and thus make the patient suffer unnecessary pain if his tooth to treat is vital. For this purpose, for example, flexible pellets of polyurethane on the basis of polyether have been used which have volumetric weight of about 20 kg/m$^3$ and a number of pores of about 25 ± 2/cm$^2$. After their impregnation with difluorodichloroethane, these pellets lead to a decrease of temperature of 50°C within 0.8 seconds on the tooth surface during the examination by touch. Thermometrical tests in vitro carried out by means of the Servogor-II-compensation recorder show that heat is withdrawn from the tooth surface during about 15 seconds. Those pellets have the drawback that they must be reimpregnated with the cold-producing agent after a relatively short time. Moreover, pellets of polyurethane on the basis of polyether show a disagreeable static charge which leads to the coagulation of the pellets.

Now, it has been found that the use of cellular plastics material having a volumetric weight of 25 to 40 kg/m$^3$ and the number of pores of 10 to 20/cm allows to treat the double number of teeth in comparison with a pellet having the same volumetric weight and being impregnated with the same amount of cold-producing agent.

Cellular plastics materials suitable for pellets in accordance with the invention are those which have a volumetric weight of from 25 to 40 kg/m$^3$, especially from 30 to 35 kg/m$^3$, preferably of 33 kg/m$^3$. Their number of pores is between about 10 to 20, preferably, within the range of from 15 to 19, especially about 17 ± 2/cm. A cellular plastics material of polyurethane on the basis of polyester (Moltopren, registered trademark) made from tolylene diisocyanate and hydroxyl terminated polyesters proved to be especially suitable. When using this special cellular plastics material, especially good results have been obtained if it had a volumetric weight of about 33 kg/m$^3$ and a number of pores of about 17 ± 2/cm. This material surprisingly did not show the coagulations occuring with known pellets.

It is also surprising that the pellets of the invention manufactured from an elastic soft cellular plastics material with open pores allow to treat a greater number of teeth, as it could be expected on account of the number of pores that the cold-producing agent would evaporate more rapidly as compared with the known pellets.

The pellets of the invention may especially be used for the treatment of teeth. They are, however, also suitable for treating tumefactions, traumatic skin and muscle irritations, and other, on the skin and mucous membrane.

Suitable cold-producing agents are, especially, halogen alkanes, for example, monofluorotrichloromethane, difluorodichloromethane, tetrafluorodichloroethane (Frigene, registered trade mark) or, for example, carbon dioxide snow. Especially because of the absence of coagulation, cellular plastics material of polyurethane on the basis of polyester is suitable. Other cellular plastics materials, for example, gelatine sponge, oxycellulose sponge or a polyurethane sponge on the basis of polyether may also be used.

The cellular plastics materials are manufactured in known manner. In the case of polyurethane sponges, for example, carbon dioxide obtained from the polyisocyanate component by the addition of water which causes foaming, is used.

Figure 2:
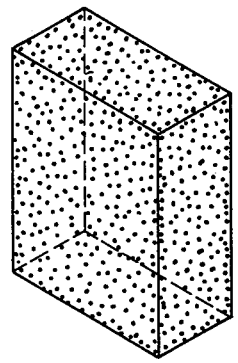
Figure 3:
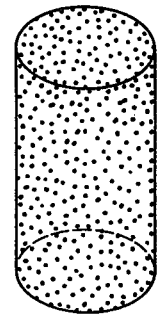

The pellets may be manufactured in various forms. Their size must be adapted to the tooth to treat and must be dimensioned in such a manner that the adjacent teeth are not wetted with the cold-producing agent. The pellets, advantageously, are in the form of a column, their ground area advantageously being of trapezoidal shape (cf. FIG. 1). The pellets of the invention may also be given a rectangular column form (cf. FIG. 2) which is about 8 mm high and the side lengths of its ground area are about 6 and 3 mm. If the ground area is of trapezoidal shape (FIG. 1), the trapezoid may, for example, be about 8 mm high, and parallel sides about 3 and 7 mm long. A column shaped pellet may also have a circular ground area and it may, for example, be 6 mm high and have a diameter of about 3 – 6 mm (cf. FIG. 3). To facilitate the treatment, pellets of a trapezoidal shaped ground area are preferred.

The pellets are used in such a manner that they are held by means of a forceps and sprayed with the cold-producing agent, preferably from an Aerosol bottle so long (for about 3 seconds) at a distance of about 2 cm, until drops fall down which prove the maximal saturation of the pellets. They are, then, promptly pressed against the tooth to examine.

What is claimed is:

1. A halocarbon impregnated pellet of an elastic soft cellular plastic material having open pores of a volumetric weight from 25 to 40 kg/m$^3$ and having a number of pores from 10 to 20/cm suitable for determining the vitality of tooth pulpa.

2. A halocarbon impregnated pellet as defined in claim 1, of a soft cellular plastic material of a volumetric weight of 33 kg/m$^3$ having a number of pores of 17 ± 2/cm.

3. A halocarbon impregnated pellet as defined in claim 1, of a cellular plastic material consisting of a polyester polyurethane.

4. In a method for determining the vitality of tooth's pulpa, the steps comprising:
impregnating with a halocarbon a pellet of an elastic soft cellular plastic material having open pores of a volumetric weight from 25 to 40 kg/m$^3$ and having a number of pores from 10 to 20 per centimeter; touching said tooth with said pellet; and observing for signs of vitality of said pulpa.

* * * * *